(12) United States Patent
Carlton et al.

(10) Patent No.: US 10,201,629 B2
(45) Date of Patent: Feb. 12, 2019

(54) CONTAINER SYSTEM

(71) Applicants: Keith Carlton, Palgrave (CA); Oliver Carlton, Palgrave (CA); Hannah Carlton, Palgrave (CA)

(72) Inventors: Keith Carlton, Palgrave (CA); Oliver Carlton, Palgrave (CA); Hannah Carlton, Palgrave (CA)

( * ) Notice: Subject to any disclaimer, the term of this patent is extended or adjusted under 35 U.S.C. 154(b) by 53 days.

(21) Appl. No.: 15/490,122

(22) Filed: Apr. 18, 2017

(65) Prior Publication Data
US 2018/0296717 A1 Oct. 18, 2018

(51) Int. Cl.
*B65D 77/00* (2006.01)
*A61L 9/12* (2006.01)

(52) U.S. Cl.
CPC ................................ *A61L 9/12* (2013.01)

(58) Field of Classification Search
USPC ...... 206/457, 0.5, 315.1, 216; 220/847, 805; 239/34, 53, 54, 55, 56
See application file for complete search history.

(56) References Cited

U.S. PATENT DOCUMENTS

| | | | | |
|---|---|---|---|---|
| 4,483,095 A | * | 11/1984 | Webinger | A01M 1/02 206/525 |
| 6,357,260 B1 | * | 3/2002 | Lutz | A44C 11/002 206/6.1 |
| 6,398,127 B1 | * | 6/2002 | Wingo | A61L 9/03 239/53 |
| 6,746,521 B2 | * | 6/2004 | Canfield | A61L 9/12 239/56 |
| 6,767,521 B1 | * | 7/2004 | Vogt | A61L 9/012 206/0.5 |
| 6,857,579 B2 | * | 2/2005 | Harris | A01M 1/2044 239/211 |
| 6,880,765 B2 | * | 4/2005 | Tuomikoski | A01M 31/008 239/34 |
| 2007/0163895 A1 | * | 7/2007 | Kirby | A45D 33/26 206/0.5 |

* cited by examiner

*Primary Examiner* — Jacob K Ackun

(57) ABSTRACT

A container system having a container assembly including a lid having a fastener and an attacher, and a container having a first-cavity, and a second-cavity. A multi-purpose container system having internal cavities for varying purposes. The second-cavity having an inner volume suitable for removably containing at least one item including a scented-item for providing air freshening via ventilated perforations for odor eliminating.

17 Claims, 6 Drawing Sheets

CONTAINER SYSTEM

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. Field of the Invention

The present invention relates generally to the field of containers and more specifically relates to a container system.

2. Description of Related Art

Air freshening or deodorizing has long been sought by consumers, in both residential and commercial environments. Due to the wide variety of odors which are generated, the desire to reduce or eliminate offensive odors has long existed along with the desire to provide a long-lasting pleasing odor. In an attempt to meet the demand for air fresheners or deodorizers, numerous products have been developed and are presently available in the marketplace. In general, these prior art products are sold as solids, liquids, or aerosol sprays to provide the desired air freshening or deodorizing effect. Typically, these prior art products are used to eliminate, chemically change, or mask an existing odor. In addition, these products typically work by absorbing odorous molecules, dissolving or emulsifying such molecules, or killing bacteria that causes the offensive odor. Although substantial effort has been expended in providing various delivery systems for establishing a pleasant odor in areas or environments in which offensive odors continuously exist, no fully satisfactory delivery system has been attained which is capable of providing portable long-term deodorizing or air freshening. A suitable solution is desired.

U.S. Pat. No. 549,043 to George Draper Worswick relates to a ventilating fruit box. The described ventilating fruit box includes a fruit box or crate which enables the top and bottom of the packed or stored fruit or articles to be readily inspected through the medium of two readily removable and replaceable covers having ventilating openings of any suitable form. The horizontal wall of the top cover. is formed with an approximately circular opening of large dimensions, formed in its edge at regular intervals with notches, as at. this enlarged central opening serves to view the upper layer of fruit or other perishable articles packed or stored in the box or crate, and said opening is designed to be closed through the medium of a secondary lid, having numerous perforations, as at, and constructed at its edge or periphery with numerous perforations, adapted to register and engage with the notches in the edge of the enlarged opening in the horizontal body portion of the top cover. the secondary lid may be provided with any suitable handle for the purpose of removing and replacing the same. The handle in the present instance is simply a piece of ribbon tied to the lid.

BRIEF SUMMARY OF THE INVENTION

In view of the foregoing disadvantages inherent in the known container art, the present disclosure provides a novel container system. The general purpose of the present disclosure, which will be described subsequently in greater detail, is to provide a multi-purpose modular container system having internal cavities for varying purposes.

A container system is disclosed herein. The container system includes a container system having a container assembly including a lid having a fastener and an attacher, and a container having a first-cavity and a second-cavity. The container system comprises the container assembly. The container assembly comprises the lid and the container in functional combination. The lid comprises a fastener. The container may comprise the first-cavity and the second-cavity in functional combination.

The lid may be removably couplable to the container. The lid may be able to fit into the first-cavity of the container. An outside wall of the container comprises ventilated perforations to emit scents of a scented-item contained within. Scented items may include wax, scented beads or other suitable items. The second-cavity may comprise an inner volume suitable for removably containing at least one item which may include the scented-item for providing air freshening via the ventilated perforations for odor eliminating.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a container system, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to a container and more particularly to a container system.

Generally speaking, the invention is a multipurpose container assembly comprising of at least two pieces, a container and a lid; the container having internal cavities of varying purposes. One cavity type is open and contained by the lid and used to mold and store a molded wax or soap bar or contain a separately molded wax bar or soap. The cavity may also be used to contain spare parts for relevant sporting activities or other products such as tobacco, candy, or coins. The second cavity type is not sealed by the lid. It may be vented through the outer wall of container and hold products intended to emit scent for the purpose of freshening. The lid comprises multiple items including a lid, a lace, fabric, or rope hinge attached to the container at one end and having an opening closing mechanism on the other end to close the container.

Figure 1:
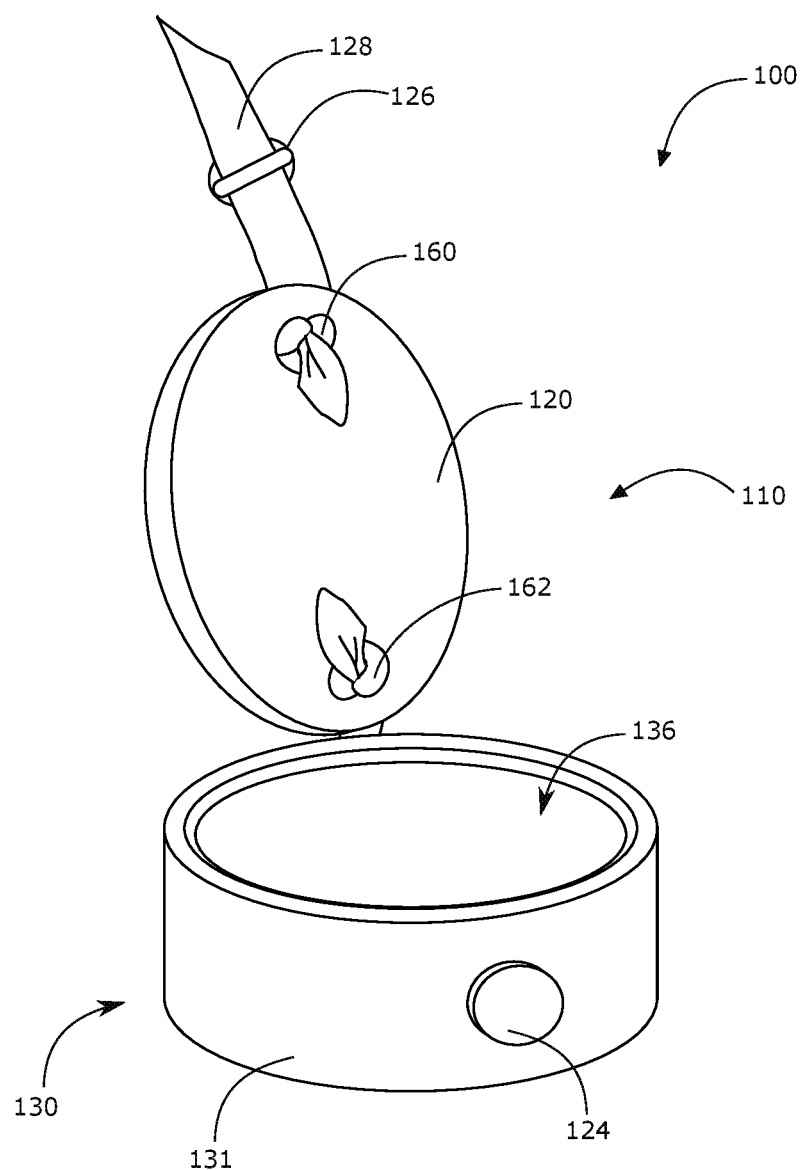
FIG. 1 is a front perspective view of the container system during an 'in-use' condition, according to an embodiment of the disclosure.

Referring now more specifically to the drawings by numerals of reference, there is shown in FIGS. 1-5, various views of a container system 100. FIG. 1 shows a container system 100 during an 'in-use' condition, according to an embodiment of the present disclosure. As illustrated, the container system 100 may include a container assembly 110 including a lid 120 having an attacher 128 and a container 130 having a second-cavity 134 (shown in FIG. 2 and not shown in FIG. 1) and a first-cavity 136. The container assembly 110 comprises the lid 120 and the container 130 in functional combination. The lid 120 comprises an attacher 128 and a female snap fastener 126. The container 130 comprises the second-cavity 134 and the first-cavity 136 in functional combination. The lid 120 may be removably couplable to and fit into the container 130. The second-cavity 134 comprises ventilated perforations 138 (shown in FIG. 2 and not shown in FIG. 1) to emit scents of a scented-item 10 (FIG. 4) contained within the second-cavity 134. The second-cavity 134 may be configured concentrically around the first-cavity 136 about an inside periphery of the container 130 and concentrically inside of the outer wall 131. The second-cavity 134 may comprise an inner volume suitable for removably containing at least one item that may include the scented-item 10 for providing air freshening via the ventilated perforations 138 (FIG. 2) for odor eliminating.

Figure 2:
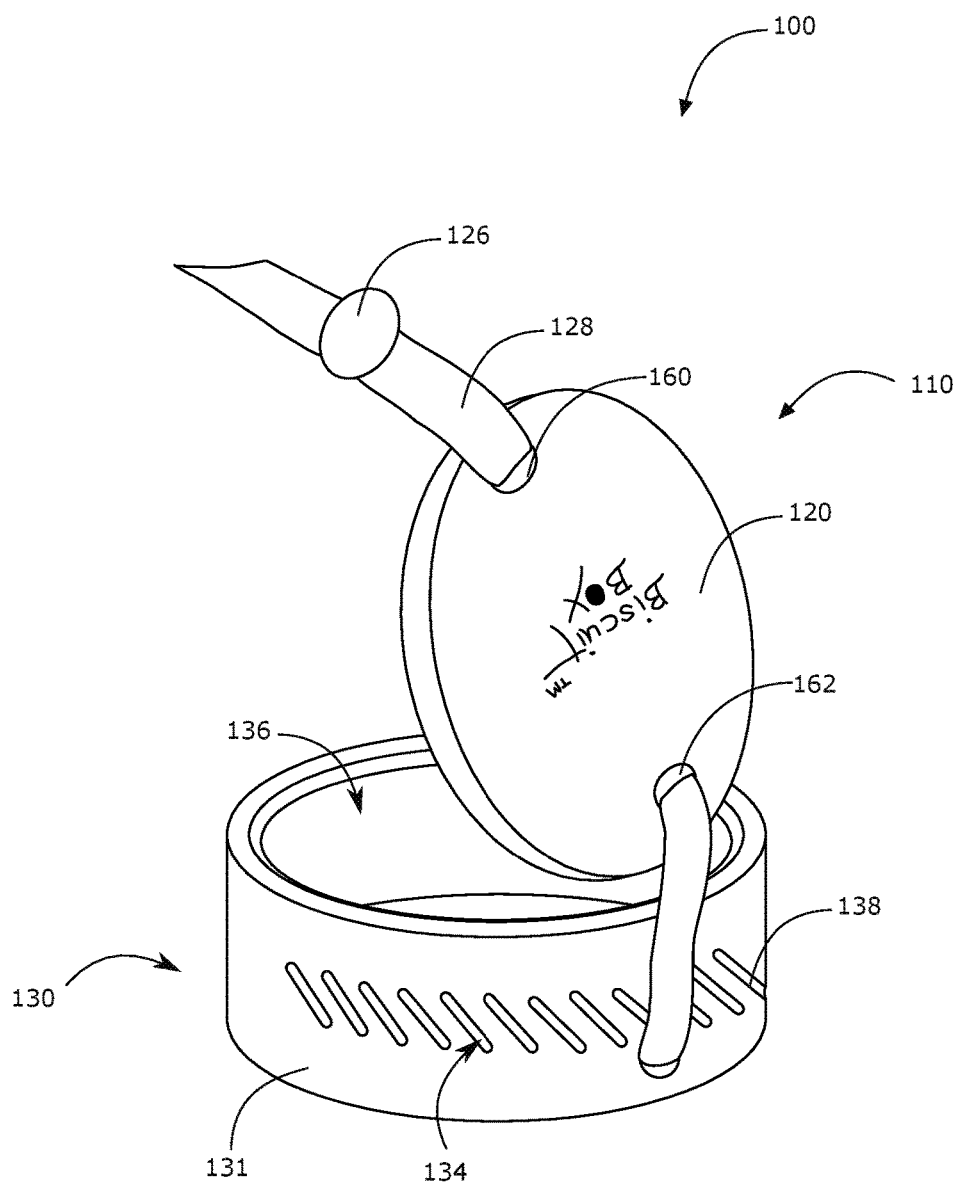
FIG. 2 is a rear perspective view of the container system of FIG. 1, according to an embodiment of the present disclosure.

FIG. 2 shows a rear perspective view of the container system 100 of FIG. 1, according to an embodiment of the present disclosure. As above, the container system 100 may include a container assembly 110 including a lid 120 having an attacher 128 with a female snap fastener 126 and a container 130 having a second-cavity 134 and a first-cavity 136. A fastener may comprise a male snap-fastener 124. The attacher 128 may comprise a flexible rope, lace, fabric string, or other suitable fastening means. In a preferred embodiment the lid 120 comprises a first-aperture 160 and a second-aperture 162 for passing and looping the attacher 128 through the apertures and fastening the lid 120 to the container 130. The lid 120 is hingedly coupled to the container 130 via the attacher 128.

Figure 3:
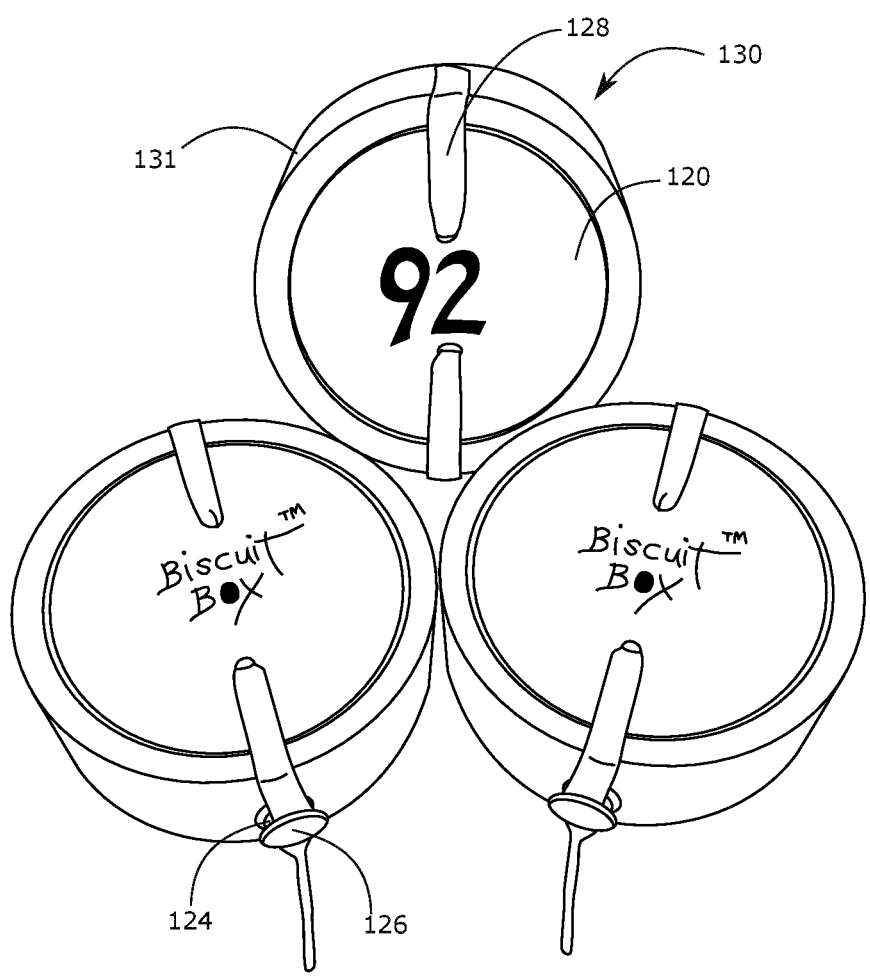
FIG. 3 is a front perspective view of the container system of FIG. 1, according to an embodiment of the present disclosure.

FIG. 3 shows a front perspective view of the container system 100 of FIG. 1, according to an embodiment of the present disclosure. As above, the container system 100 may include a container 130 supporting a male snap-fastener 124. When in a closed position, the male snap-fastener 124 can couple to the female snap-fastener 126. Male snap-fastener 124 is located on an outer wall 131 of the container 130. The second-cavity 134 and the first-cavity 136 comprise a cylindrical body. The container assembly 110 comprises customizable indicia. Indicia may include various designs for a plurality of activities and may aid the function of the present invention. The device may also use indicia to indicate ownership. The device may be manufactured in various shapes including a hockey puck. The color of the container, lid graphics, hinge design, and ventilated perforation 138 design may all be customized. The lid 120 comprises a lid-circumference smaller than that of the outer wall 131 and greater than that of the first-cavity 136 allowing the lid 120 to rest on the container 130 when in a closed position.

Figure 4:
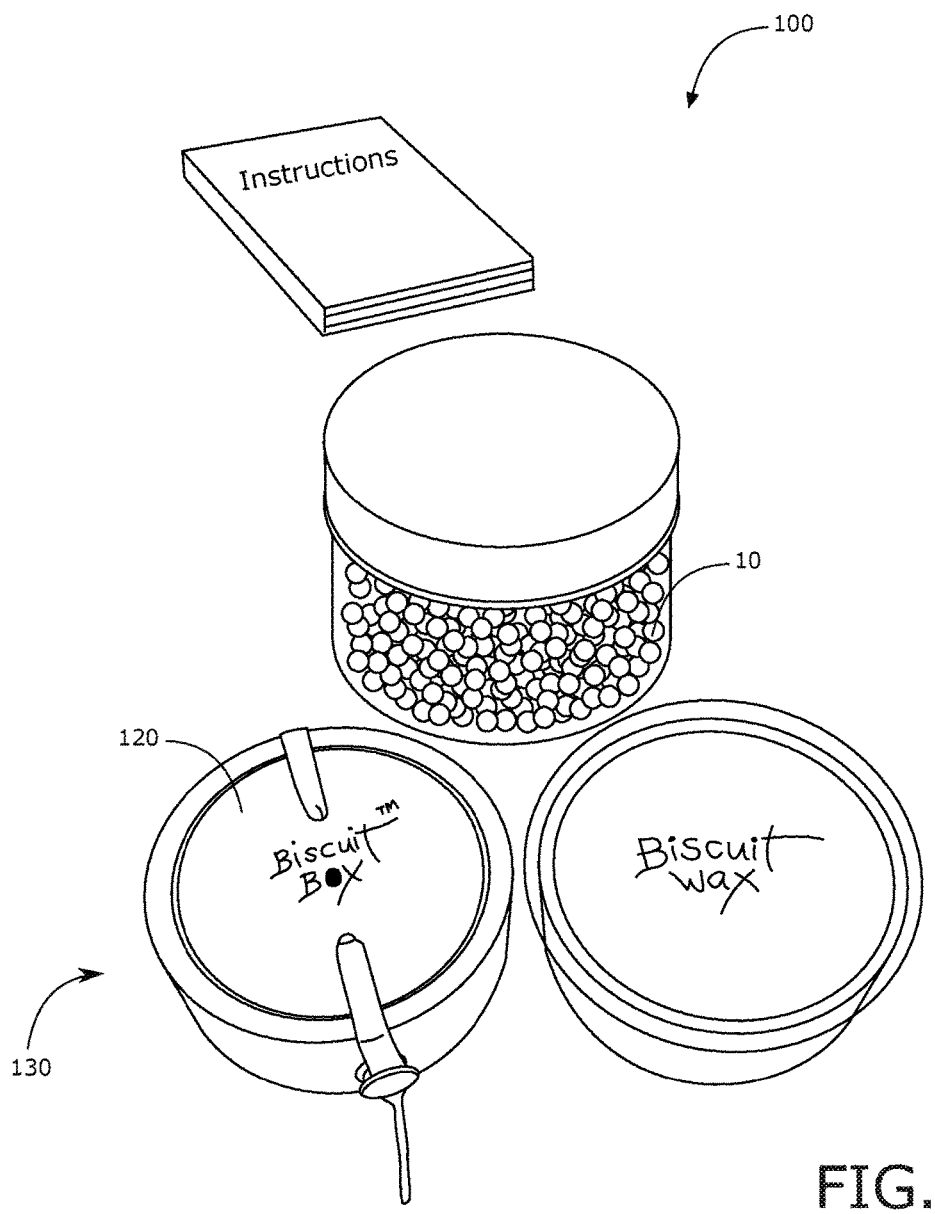
FIG. 4 is a front perspective view of the container system of FIG. 1, according to an embodiment of the present disclosure.

FIG. 4 shows a front perspective view of the container system 100 of FIG. 1, according to an embodiment of the present disclosure. As above, the container system 100 may include a first-cavity 136 that is able to mold and store a molded wax or soap. The first-cavity 136 is preferably thermal resistant allowing a user to pour hot wax directly inside the first-cavity 136 for molding and storing. The first-cavity 136 removably contains at least one item including a non-scented-item or a scented item. The at least one item comprises sporting equipment such as wax, helmet snaps, screws, sharpening stones or other loose products such as chewing tobacco, candy or coins. The ventilated perforations 138 connect the second-cavity 134 to the outer surface of container 130. The device may be used for freshening a surrounding environment such as a sporting equipment bag.

Figure 5:
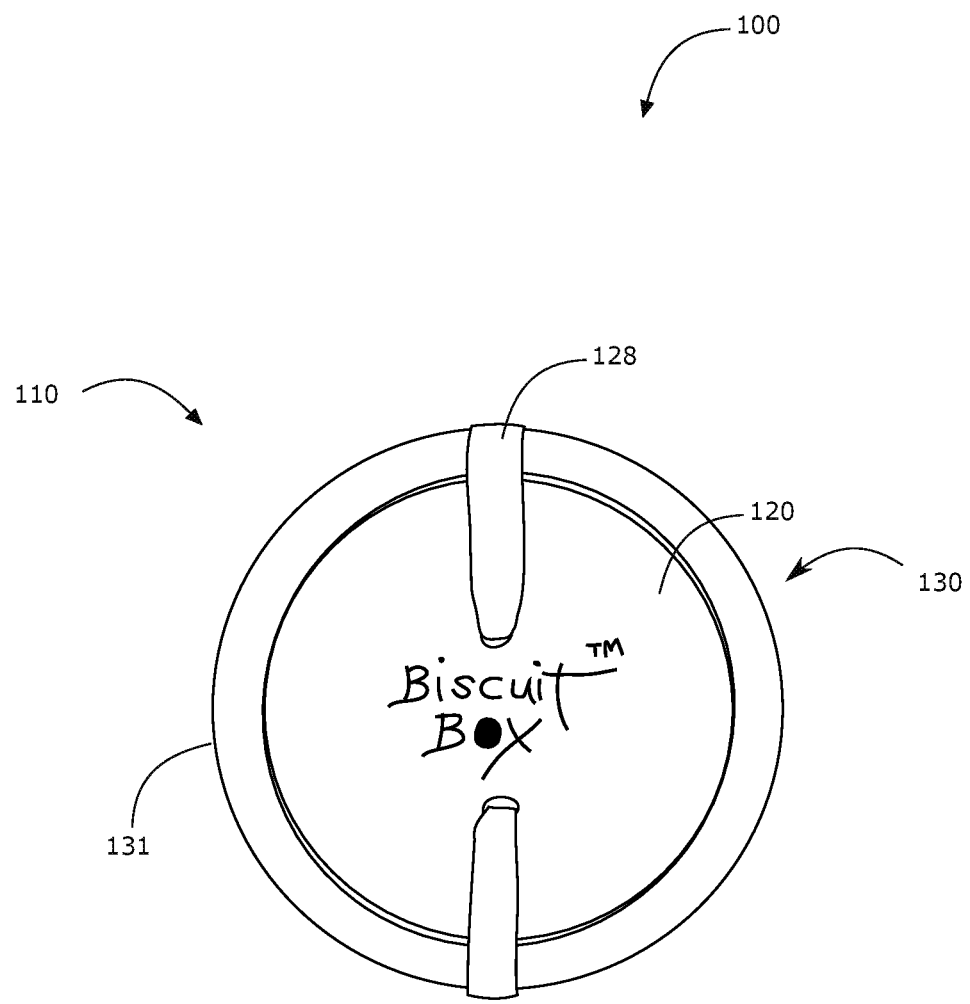
FIG. 5 is a perspective view of the container system of FIG. 1, according to an embodiment of the present disclosure.

FIG. 5 shows a perspective view of the container system 100 of FIG. 1, according to an embodiment of the present disclosure. As above, the container system 100 may include a container assembly 110 including a lid 120 having a fastener, such as a snap fastener 124, and an attacher 128, and a container 130 having a first-cavity 136 and a second-cavity 134. Other fastening or attaching means may be used.

Figure 6:
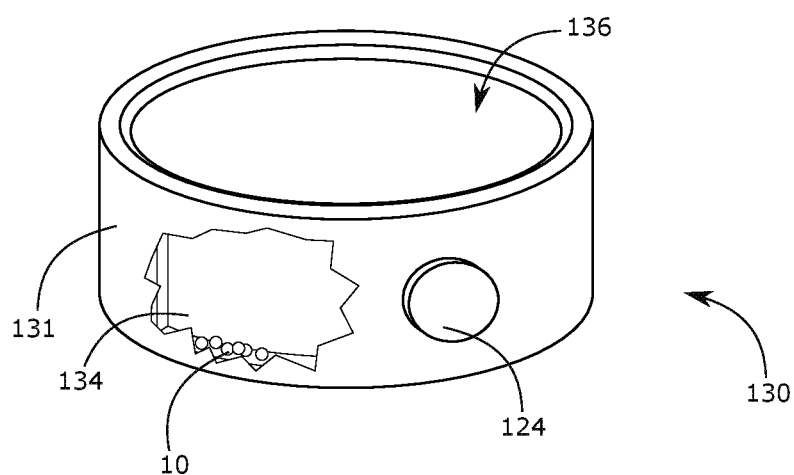
FIG. 6 is a cutaway, perspective view of the container system of FIG. 1, according to an embodiment of the present disclosure.

FIG. 6 shows a cutaway, perspective view of the container system 100 of FIG. 1, according to an embodiment of the present disclosure. This view shows the container 130 with a portion of the outer wall 131 removed, revealing the second-cavity 134, which, in this embodiment, contains scented-item 10.

According to one embodiment, the container system 100 may be arranged as a kit. The kit may include at least one scented item 10, a container assembly 110, and a set of user instructions 155. The instructions may detail functional relationships in relation to the structure of the container system 100 (such that the container system 100 can be used, maintained, or the like, in a preferred manner).

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A container system comprising:
   a container assembly including
      a lid having
         an attacher; and
      a container having
         a fastener;
         a first-cavity; and
         a second-cavity;
   wherein said container assembly comprises said lid and said container in functional combination;
   wherein said lid is removably couplable to said container;

wherein an outside wall of said container comprises ventilated perforations to emit scents of a scented-item contained within said second-cavity;
and
wherein said second-cavity comprises an inner volume suitable for removably containing at least one item including said scented-item.

2. The container system of claim 1, wherein said fastener comprises a male snap-fastener.

3. The container system of claim 1, wherein said attacher comprises a flexible rope.

4. The container system of claim 3, wherein said lid comprises a first-aperture and a second-aperture for passing and looping said attacher through said apertures and fastening said lid to said container.

5. The container system of claim 1, wherein said lid is hingedly coupled to said container via said attacher.

6. The container system of claim 1, wherein said attacher supports a female snap-fastener.

7. The container system of claim 1, wherein said container supports a male snap-fastener.

8. The container system of claim 1, wherein when said container assembly is in a closed position said female snap-fastener is able to couple to said male snap-fastener.

9. The container system of claim 1, wherein said first-cavity and said second-cavity comprise a cylindrical body.

10. The container system of claim 1, wherein said container assembly comprises customizable and functional indicia.

11. The container system of claim 1, wherein said lid comprises a lid-circumference smaller than a circumference of an outer wall and greater than a circumference of said second-cavity.

12. The container system of claim 1, wherein said first-cavity is able to mold and store a molded wax.

13. The container system of claim 1, wherein said first cavity is thermal resistant to allow a user to pour hot wax directly inside said first cavity for molding and storing.

14. The container system of claim 1, wherein said first-cavity removably contains at least one item including a non-scented-item.

15. The container system of claim 12, wherein said at least one item comprises sporting equipment.

16. The container system of claim 1, wherein said ventilated perforations connect the second-cavity to the outside wall.

17. A container system comprising:
a container assembly including
a lid having
an attacher; and
a container having
a fastener;
a first-cavity; and
a second-cavity;
wherein said container assembly comprises said lid and said container in functional combination;
wherein said fastener comprises a male snap-fastener;
wherein said lid is removably couplable to said container;
wherein said first-cavity removably contains at least one item including a non-scented-item;
wherein said second-cavity comprises ventilated perforations that connect the second-cavity to the outside wall; and
wherein said second-cavity comprises an inner volume suitable for removably containing at least one item including a scented-item.

* * * * *